United States Patent
Cifter et al.

(10) Patent No.: US 10,111,925 B2
(45) Date of Patent: Oct. 30, 2018

(54) FORMULATIONS COMPRISING PLANT EXTRACTS

(71) Applicant: MONTERO GIDA SANAYI VE TICARET A.S., Istanbul (TR)

(72) Inventors: Ümit Cifter, Istanbul (TR); Nazife Arabacioglu, Istanbul (TR); Özlem Toker, Istanbul (TR)

(73) Assignee: MONTERO GIDA SANAYI VE TICARET A.S., Istanbul (TR)

( * ) Notice: Subject to any disclaimer, the term of this patent is extended or adjusted under 35 U.S.C. 154(b) by 562 days.

(21) Appl. No.: 14/436,351

(22) PCT Filed: Oct. 17, 2013

(86) PCT No.: PCT/EP2013/071766
§ 371 (c)(1),
(2) Date: Apr. 16, 2015

(87) PCT Pub. No.: WO2014/060539
PCT Pub. Date: Apr. 24, 2014

(65) Prior Publication Data
US 2015/0273009 A1  Oct. 1, 2015

(30) Foreign Application Priority Data

Oct. 18, 2012 (TR) ................................. 2012 12023
Oct. 18, 2012 (TR) ................................. 2012 12042
Oct. 18, 2012 (TR) ................................. 2012 12044

(51) Int. Cl.
| | |
|---|---|
| A61K 36/28 | (2006.01) |
| A61K 36/9066 | (2006.01) |
| A61K 36/185 | (2006.01) |
| A61K 36/9068 | (2006.01) |
| A61K 35/644 | (2015.01) |
| A61K 36/25 | (2006.01) |
| A61K 47/10 | (2017.01) |
| A61K 9/00 | (2006.01) |
| A61K 36/484 | (2006.01) |
| A61K 45/06 | (2006.01) |

(52) U.S. Cl.
CPC ........ *A61K 36/9068* (2013.01); *A61K 9/0095* (2013.01); *A61K 35/644* (2013.01); *A61K 36/185* (2013.01); *A61K 36/25* (2013.01); *A61K 36/28* (2013.01); *A61K 36/484* (2013.01); *A61K 45/06* (2013.01); *A61K 47/10* (2013.01)

(58) Field of Classification Search
None
See application file for complete search history.

(56) References Cited

U.S. PATENT DOCUMENTS

| | | | |
|---|---|---|---|
| 5,904,924 A | 5/1999 | Gaynor et al. | |
| 7,211,567 B1* | 5/2007 | Kotani | A61K 31/7048 424/439 |
| 8,653,135 B1* | 2/2014 | Dixit | A61K 45/06 514/561 |
| 2004/0126441 A1 | 7/2004 | Pushpangadan et al. | |
| 2009/0155189 A1* | 6/2009 | Kovacs | A61K 9/006 424/48 |
| 2010/0112096 A1* | 5/2010 | Herrmann | A61K 36/185 424/725 |
| 2011/0081434 A1* | 4/2011 | Auh | A61K 36/25 424/773 |
| 2015/0273003 A1 | 10/2015 | Cifter et al. | |
| 2015/0290253 A1 | 10/2015 | Cifter et al. | |
| 2015/0290268 A1 | 10/2015 | Cifter et al. | |

FOREIGN PATENT DOCUMENTS

| | | | |
|---|---|---|---|
| BE | 780165 A | * | 1/1972 |
| CH | 676931 A5 | | 3/1991 |
| CN | 10131893 A | * | 12/2008 |
| CN | 101637347 A | | 2/2010 |
| CN | 101695563 A | | 4/2010 |
| CN | 102100900 A | * | 6/2011 |
| CN | 102100900 A | | 6/2011 |
| CN | 102258614 A | * | 11/2011 |
| CN | 102343077 A | | 2/2012 |
| CN | 102698233 A | | 10/2012 |
| DE | 4211745 A1 | | 10/1993 |
| EP | 1520584 A1 | | 4/2005 |
| EP | 1829548 A1 | | 9/2007 |
| HU | 75540 T | * | 5/1997 |
| WO | WO-2009/011498 A1 | | 1/2009 |
| WO | WO2012049045 A1 | * | 4/2012 |
| WO | WO-2012/084075 A1 | | 6/2012 |
| WO | WO-2014/060525 A1 | | 4/2014 |
| WO | WO-2014/060529 A1 | | 4/2014 |
| WO | WO-2014/060533 A1 | | 4/2014 |

OTHER PUBLICATIONS

Aimbire et al., "Effect of hydroalcoholic extract of Zingiber officinalis rhizomes on LPS-induced rat airway hyperreactivity and lung inflammation," Prostaglandins Leukot Essent Fatty Acids. 77(3-4):129-38 (2007).

(Continued)

*Primary Examiner* — Christopher R Tate
*Assistant Examiner* — Randall Winston
(74) *Attorney, Agent, or Firm* — Kilpatrick Townsend & Stockton LLP

(57) ABSTRACT

The present invention is related to a formulation comprising *Hedera helix*, *Pelargonium sidoides*, and *Zingiber officinale* extracts to be used in the treatment, prevention of various respiratory diseases or alleviation and/or elimination of symptoms thereof and a method for preparing said formulation.

22 Claims, No Drawings

(56) References Cited

OTHER PUBLICATIONS

Cohen et al., "Effectiveness of an herbal preparation containing echinacea, propolis, and vitamin C in preventing respiratory tract infections in children: a randomized, double-blind, placebo-controlled, multicenter study," Arch Pediatr Adolesc Med. 158(3):217-21 (2004).
Fazio et al., "Tolerance, safety and efficacy of Hedera helix extract in inflammatory bronchial diseases under clinical practice conditions: a prospective, open, multicentre postmarketing study in 9657 patients," Phytomedicine. 16(1):17-24 (2009).
Hofmann et al., "Efficacy of dry extract of ivy leaves in children with bronchial asthma—a review of randomized controlled trials," Phytomedicine. 10(2-3):213-20 (2003).
International Preliminary Report on Patentability for PCT Application No. PCT/EP2013/071741, dated Apr. 21, 2015 (6 pages).
International Preliminary Report on Patentability for PCT Application No. PCT/EP2013/071750, dated Apr. 21, 2015 (7 pages).
International Preliminary Report on Patentability for PCT Application No. PCT/EP2013/071758, dated Apr. 21, 2015 (6 pages).
International Preliminary Report on Patentability for PCT Application No. PCT/EP2013/071766, dated Apr. 21, 2015 (6 pages).
International Search Report and Written Opinion for PCT Application No. PCT/EP2013/071741, dated Jan. 23, 2014 (9 pages).
International Search Report and Written Opinion for PCT Application No. PCT/EP2013/071750, dated Jan. 23, 2014 (11 pages).
International Search Report and Written Opinion for PCT Application No. PCT/EP2013/071758, dated Jan. 23, 2014 (9 pages).
International Search Report and Written Opinion for PCT Application No. PCT/EP2013/071766, dated Jan. 23, 2014 (10 pages).
Kemmerich et al., "Efficacy and tolerability of a fluid extract combination of thyme herb and ivy leaves and matched placebo in adults suffering from acute bronchitis with productive cough. A prospective, double-blind, placebo-controlled clinical trial," Arzneimittel Forschung./Drug Research. 56(9):652-60 (2006).
Matthys et al., "Efficacy and safety of an extract of Pelargonium sidoides (EPs 7630) in adults with acute bronchitis. A randomised, double-blind, placebo-controlled trial," Phytomedicine. 10(Suppl 4):7-17 (2003).
Matthys et al., "Pelargonium sidoides preparation (EPs 7630) in the treatment of acute bronchitis in adults and children," Phytomedicine. 14(Suppl 6):69-73 (2007).
Search Report and Written Opinion for Turkish Application No. TR201212043, dated Jul. 18, 2013 (18 pages).
Search Report and Written Opinion for Turkish Application No. TR201212044, dated May 14, 2013 (9 pages).

* cited by examiner

FORMULATIONS COMPRISING PLANT EXTRACTS

FIELD OF THE INVENTION

The present invention is related to a new formulation comprising *Hedera helix* extract, *Pelargonium sidoides* extract, and *Zingiber officinale* extract.

The present invention is also related to a method used for the preparation of a formulation comprising *Hedera helix*, *Pelargonium sidoides*, and *Zingiber officinale* extracts and use of said formulation in mammals, especially, in humans, for treatment, prevention of a variety of respiratory diseases or alleviation and/or elimination of symptoms thereof.

BACKGROUND OF THE INVENTION

In recent years, the use of various herbs and/or herbal medical products for the prevention of disease, alleviating the effects thereof, or for treating diseases have been gradually increasing in all societies. Throughout the human history, there have been and still are attempts for treating many diseases (diabetes, jaundice, dyspnea, etc.) by using some herbs. According to the records of the World Heath Organization (WHO), a large proportion of the world's population (70-80%) makes use of herbs for therapeutic or prophylactic purposes. Additionally, around 25% of prescription drugs in developed countries are composed of plant based active agents (vinblastine, reserpine, quinine, aspirin, etc.) (Farnsworth et al., 1985).

Particularly following the end of the 1990s, the discovery of new areas of use for medical and aromatic herbs and the increasing demand for natural products have increased the use potential thereof day by day.

Herbal medical products have long been widely used for the treatment or prophylaxis of respiratory diseases. In the treatment or prophylaxis of these diseases which are typically caused by viruses, bacteria, and/or fungi, it is quite significant both to eradicate these harmful organisms and to boost the immune system of the affected individual. This is because the immune system is comprised of processes providing protection against diseases, as well as recognizing and eliminating the pathogenic and tumor cells in a living being. The system scans the organism against any kind of foreign substances, entering or contacting the former, from viruses to parasitic worms of a wide variety, and distinguishes them from the organism's own healthy cells and tissues. The immune system can even distinguish substances with very similar features from each other to such an extent that even proteins having a different amino acid can be distinguished from the equivalents thereof. The function of the immune system is primarily to prevent harmful foreign substances from entering the respective organism, or upon entry, to retain the substances at the place of entry, or to prevent or delay their spreading therein.

*Hedera helix* (English Ivy) is one of the plant species used in the production of herbal products for the treatment and prevention of diseases, and/or for the alleviation and/or elimination of the symptoms thereof. *Hedera helix*, comprising saponins, phenol, and alkaloids, is known to be used for the treatment of cough, parasites, skin diseases, bronchitis, and chronic respiratory tract diseases. Various studies have been performed to demonstrate the effect of *Hedera helix* on said diseases. For instance, Erik van Wyk and Michael Wink stated in "Medicinal Plants of the World" that the expectorant action of *Hedera Helix* works by stimulating the "nervus vagus" in the stomach, causing a cough response. A study by S. Fazio et al. published in the January 2009 issue of "Phytomedicine" tested a dried leaf extract on 9657 patients with acute and chronic bronchitis, including children. Accordingly, it was observed that following one week, cough and chest pain disappeared or improved in 95% of patients.

*Pelargonium sidoides* (African Geranium, Umckaloabo) is a plant species widely used in the treatment and prevention of, or in the alleviation and/or elimination of the symptoms of cold and respiratory tract disease (pharyngitis, sinusitis, acute bronchitis, tonsillitis). It was determined to be effective in increasing the generation of natural killer cells and tumor necrosis factor alpha, and to enhance the release of interferon beta. *Pelargonium sidoides* has antiviral properties strengthening the immune system. It further has both antibacterial effects and antioxidative properties against some bacteria. Apart from that, it was also reported to boost the immune system of the respective organism and to have expectorant action by increasing the ciliary beat frequency of respiratory epithelial cells. In a multicenter study conducted by the Pneumology Department of a German University Hospital (2000) on acute bronchitis patients, including adults, children, and infants, it was determined that an extract of the roots of *Pelargonium sidoides* reduced the severity of the symptoms after 7 days treatment from 6.3 to 0.9 according to the average bronchitis severity score. A study published in "Acta Paediatrica" in April 2010, showed that preparations extracted from herbal roots were much more effective in the treatment of acute bronchitis as compared to placebo. A study group of children aged 6 to 18 years, taking the herbal extracts experienced less coughing, sputum, and bed rest times versus placebo. By assessing the results of four placebo-controlled clinic trials, the researchers at the Medical Center, the University of Pittsburgh, concluded that a standardized extract of *Pelargonium sidoides* showed a much better performance in alleviating the bronchitis symptoms versus placebo in a 7-day treatment period.

Ginger, *Zingiber officinale*, is also called "warming herb" and used for a long time as an important medical herb. It comprises essential oils with ether comprising Zingiberene, Zingiberol, Gingerol and Shogol. The essential oils contained which are mixed with terpenoids give the special taste and scent of ginger. The bitter substances without essential oils which make the mouth feel warm are gingerol and zingeron.

Ginger has a wide area of usage. Ginger is preventive against cancer based on stopping the Epstein-barr virus activity. 6-gingerol and 6-paradol, among the active substances of ginger, are effective in stopping promyelocytic leucaemia by disturbing the DNA synthesis. It also has anti-inflammatory effect, is effective against arthritis and headache, and is bacteriostatic. It is used against nausea, spasm and fever in kids. Based on its antiseptic effect, it is used against stomach and intestine infections and even against food poisoning. It also prevents the coagulation of the blood and has blood thinning effect. It supports the cardiovascular system by making the platelets less adherent, this in turn causes a decrease in the problems of circulation system. It is appetizing and can also be used against constipation. In addition to these, it has a warming and sedative effect in cough, flu, cold and other respiratory system diseases.

In prior art, there are many formulations, which comprises herbal agents or combinations of herbal agents, are disclosed. For example, WO2009/011498 A1 discloses a composition for the treatment of infection in the form of a syrup comprising *Pelargonium sidoides*; EP1829548 A1 discloses a composition comprising an extract of *Pelargonium sidoides*; KEMMERICH BERND at al.: "Efficiency and tolerability of a fluid extract combination of thyme herb and ivy leaves and matched placebo in adults suffering from acute bronchitis with productive cough. A prospective, double-blind, placebo-controlled clinical trials" (ARZNEIMITTEL FORSCHUNG. DRUG RESEARCH, Acv EDITO CANTOR VERLAG, AULENDORF, DE, vol. 56, no. 9, 1 Jan. 2006, pages 652-660) discloses the use of the combination of extracts of thyme herb and ivy leaves for the treatment of acute bronchitis; FAZIO S et al.: "Tolerance, safety and efficacy of *Hedera helix* extract in inflammatory bronchial diseases under clinical practice conditions: A prospective, open, multicenter postmarketing study in 9657 patients", (PHYTOMEDICINE, GUSTAV FISCHER VERLAG, STUTTGART, DE, vol. 16, no. 1, 2009, pages 17-24) discloses a composition in the form of a syrup comprising dried *Hedera helix* extract; HOFFMANN D et al.: "Efficacy of dry extract of ivy leaves in children with bronchial asthma—a review of randomized controlled trials", (PHYTOMEDICINE, GUSTAV FISCHER VERLAG, STUTTGART, DE, vol. 10, no. 2-3, 2003, pages 213-220) discloses a composition comprising dried ivy leaves for the treatment of chronic airway obstruction in children suffering from bronchial asthma. Although there are a large number of formulations comprising combination of herbal substance, the effects of a formulation comprising *Hedera helix* extract, *Zingiber officinale* extract and *Pelargonium sidoides* extract have been still unknown.

Products to be used for medical purposes have to incorporate the elements of quality, efficiency, and reliability. A product can be a "medical" product only by having these elements. In order for the product prepared from a herbal source to be used in medicine, it has to be prepared from an effective and a standardized extract, pharmacological, clinical outcomes and toxicological data thereof has to be established as well as stability of the product has to be determined. Therefore, it bears great significance to have a good stability for a product, produced from herbal sources, to be used in the treatment and prevention of diseases, or in the alleviation and/or elimination of the symptoms thereof.

Physical, chemical and microbiological factors play role in the stability of drugs or other products manufactured for medical purposes. The stability issue is not dependent on a simple cause only, but emerges as a result of many factors. Factors such as the interaction of active agents contained in a product, the interaction of excipients among themselves or with active agents, pH, light, humidity, and temperature are among many factors which may influence the stability of such products.

Until recently, researchers have deemed considerable importance on the chemical stability of the pharmaceutical products rather than the physical stability thereof and have conducted numerous studies on this subject. However, in many cases, they have demonstrated how the changes in the physical structure of the products are important for the quality of the product and for durability of technological, microbiological and biopharmaceutical properties thereof. Accordingly, it was shown that primarily the physical stability of a product has to be maintained in order to sustain its quality and other features thereof, and therefore ensuring the physical stability during the development of pharmaceutical products is as important as, or sometimes more important than ensuring the chemical stability thereof.

Additionally, the physical properties taken into account in the evaluation of the physical stability of a product, particularly the taste, scent, color, clarity, uniformity, etc. of a product, also considerably influence the patient compliance. For this reason, when a novel formulation is developed, besides aiming a formulation of good physical stability, the physical properties of this formulation should be made ideal to provide high patient compliance.

However, it is quite difficult to provide the above described conditions in the formulations comprising herbal substances. Due to some characteristic chemical, biological and physical properties of the herbal substances used in the formulation, some problems are encountered in obtaining a formulation comprising said substances as well as having a good physical stability and ideal physical properties in terms of patient compliance.

Physical properties and physical stability of the formulation are directly affected by the characteristic features of the herbal substances comprised therein. The herbal substance comprised in the formulation having physical properties such as a bad taste, bad scent, bad color, being easily oxidized and providing a suitable medium for reproduction of microorganisms, adversely affect the physical stability and physical properties of said formulation. Additionally, in case a formulation comprises a combination of herbal agents, a correct selection of the herbal agents bears great importance, since more than one herbal agent present in the same formulation are capable to mutually affect their respective properties.

Under the light of the foregoing, it would be desirable to provide a formulation, as well as a process for the preparation of this formulation, comprising combinations of herbal agents, being capable to retain the physical stability for a long time, and having ideal physical properties in terms of patient compliance.

In detail, there is a need in the state of art to a formulation comprising *Hedera helix* extract, *Pelargonium sidoides* extract and *Zingiber officinale* extract, and having ideal physical properties to ensure high patient compliance and good physical stability, as well as to a method for preparing this formulation, which is simple, cost-efficient and time-saving.

SUBJECT OF THE INVENTION

The main object of the present invention is to provide new formulations which comprises *Hedera helix* extract, *Pelargonium sidoides* extract, and *Zingiber officinale* extract, overcomes the above mentioned problems and have advantages over said problems.

According to this main object, formulations according to the present invention are suitable for treatment, prevention of various respiratory diseases or alleviation and/or elimination of symptoms thereof.

Another object of the present invention is to provide a formulation comprising *Hedera helix* extract, *Pelargonium sidoides* extract, and *Zingiber officinale* extract with a good physical stability.

Another object of the present invention is to provide a formulation comprising *Hedera helix* extract, *Pelargonium sidoides* extract, and *Zingiber officinale* extract with a clear and homogeneous appearance.

Another object of the present invention is to provide a formulation comprising *Hedera helix* extract, *Pelargonium sidoides* extract, and *Zingiber officinale* extract which both maintains the physical stability and has improved physical properties as a result of using suitable excipients.

Another object of the present invention is to provide a simple, cost effective and time saving process for the preparation of formulations comprising *Hedera helix* extract, *Pelargonium sidoides* extract, and *Zingiber officinale* extract.

DESCRIPTION OF THE INVENTION

The maintenance of the physical stability of a pharmaceutical product can be ensured if no change occurs in the physical structure of that product. Therefore, whether the physical stability is maintained or not is assessed by determining changes in various physical properties of the product during formulation development process. Properties such as the color, scent, taste, pH, clarity, viscosity, homogeneity, density are among the physical properties of a pharmaceutical are the basic physical properties playing role in the assessment of the physical stability thereof.

Surprisingly, in the physical stability studies conducted during development of a herbal formulation comprising *Hedera helix* extract and *Pelargonium sidoides* extract suitable for medical purposes, it is found that in the event of adding another herbal substance, *Zingiber officinale* extract, into the formulation, physical stability of the product is improved and thus, the physical properties such as the color, scent, taste, pH, clarity, viscosity, uniformity, and the density thereof at the time the formulation was prepared were maintained for a longer time such that the physical stability was maintained as well.

In other words, it is found that the physical properties of the formulation comprising *Hedera helix, Pelargonium sidoides*, and *Zingiber officinale* extracts such as the color, scent, taste, density, clarity, homogeneity, viscosity, and pH taken into account when assessing the physical stability thereof are maintained for longer periods as compared to those of the formulation comprising only *Hedera helix* and *Pelargonium sidoides* extracts.

However, again surprisingly, when more than 30% (w/v) of *Zingiber officinale* extract based on the total volume of formulation is added to the formulation comprising *Hedera helix* and *Pelargonium sidoides* extracts, it is observed that precipitation is formed. This situation adversely affects the appearance, homogeneity and clarity of the formulation. However, when less than 30% of *Zingiber officinale* extract based on the total volume of the formulation is added to the formulation according to the present invention, it is observed that no precipitation is formed. Accordingly, the present invention, in more detail, is a formulation comprising *Hedera helix, Pelargonium sidoides* and *Zingiber officinale* extracts, wherein the percentage amount of the *Zingiber officinale* extract comprised therein is less than 30% (w/v) based on the total volume of the formulation. In view of all the foregoing, the present invention provides a formulation that is both homogeneous and clear and has an improved physical stability.

According to a preferred embodiment of the present invention, the percentage amount of the *Zingiber officinale* extract contained in the formulation based on the total volume of the formulation is less than 20% (w/v), more preferably, between 0.1% and 4% (w/v), e.g. between 0.1% and 3.8%; between 0.1% and 3.5%; between 0.1% and 3.2%; between 0.1% and 3%; between 0.1% and 2.8%; between 0.1% and 2.5%; between 0.1% and 2.2%; between 0.1% and 2%; between 0.1% and 1.8%; between 0.1% and 1.5%; between 0.1% and 1.2%; between 0.1% and 1%; between 0.2% and 3.8%; between 0.2% and 3.5%; between 0.2% and 3.2%; between 0.2% and 3%; between 0.2% and 2.8%; between 0.2% and 2.5%; between 0.2% and 2.2%; between 0.2% and 2%; between 0.2% and 1.8%; between 0.2% and 1.5%; between 0.2% and 1.2%; between 0.2% and 1%; between 0.3% and 3.8%; between 0.3% and 3.5%; between 0.3% and 3.2%; between 0.3% and 3%; between 0.3% and 2.8%; between 0.3% and 2.5%; between 0.3% and 2.2%; between 0.3% and 2%; between 0.3% and 1.8%; between 0.3% and 1.5%; between 0.3% and 1.2%; between 0.3% and 1%; between 0.4% and 3.8%; between 0.4% and 3.5%; between 0.4% and 3.2%; between 0.4% and 3%; between 0.4% and 2.8%; between 0.4% and 2.5%; between 0.4% and 2.2%; between 0.4% and 2%; between 0.4% and 1.8%; between 0.4% and 1.5%; between 0.4% and 1.2%; between 0.4% and 1%; between 0.5% and 3.8%; between 0.5% and 3.5%; between 0.5% and 3.2%; between 0.5% and 3%; between 0.5% and 2.8%; between 0.5% and 2.5%; between 0.5% and 2.2%; between 0.5% and 2%; between 0.5% and 1.8%; between 0.5% and 1.5%; between 0.5% and 1.2%; between 0.5% and 1%.

Within the scope of the present invention, the percentage amount of the *Zingiber officinale* extract represents a gram-based amount of *Zingiber officinale* extract per 100 ml of formulation.

Surprisingly, in the formulation according to the present invention, when *Zingiber officinale* extract and *Hedera helix* extract are used in a specific weight ratios, i.e. when the weight ratio of the *Zingiber officinale* extract to the *Hedera helix* extract is between 1:0.1 and 1:50, a synergistic effect on the physical stability of said formulation is observed. Thus, maintenance of the quality, reliability and shelf life of the formulation for longer periods is provided with the formulation of the present invention having an improved physical stability.

Accordingly, in the formulation according to the present invention, the weight ratio of the *Zingiber officinale* extract to the *Hedera helix* extract is between 1:0.1 and 1:50, preferably between 1:0.2 and 1:25, and more preferably between 1:0.6 and 1:15.

In the formulation according to the present invention administered by oral route in the form of syrup, the percentage amount of the *Hedera helix* extract based on the total volume of the formulation is between 0.05% and 20% (w/v), preferably between 0.1% and 15% (w/v), more preferably between 0.25% and 10% (w/v); the percentage amount of the *Pelargonium sidoides* extract based on the total volume of the formulation is between 0.05% and 30% (w/v), preferably between 0.1% and 20% (w/v), and more preferably between 0.2% and 15% (w/v). Here, the percentage amount of the *Hedera helix* extract is gram-based amount of the *Hedera helix* extract contained in the 100 ml formulation; the percentage amount of the *Pelargonium sidoides* extract is gram-based amount of the *Pelargonium sidoides* extract contained in the 100 ml formulation.

In another aspect of the invention, the weight ratio of the *Hedera helix* extract to the *Pelargonium sidoides* extract contained in the formulation according to the present invention is between 1:0.1 and 1:45, preferably between 1:0.25 and 1:25, more preferably between 1:0.5 and 1:15.

In the formulations according to the present invention comprising *Hedera helix* extract, *Pelargonium sidoides* extract, and *Zingiber officinale* extract in the amount and ratios mentioned above, the taste, scent, appearance, viscosity, pH and clarity properties as compared to the formulations comprising only *Hedera helix* extract and *Pelargonium sidoides* extract does not change over longer periods and thus, physical stability is maintained for a longer duration.

In another aspect of the invention, the formulation comprising *Hedera helix* extract, *Pelargonium sidoides* extract, and *Zingiber officinale* extract can be administered by oral, parenteral, ocular, nasal, buccal, sublingual and topical route.

According to a preferred embodiment of the present invention, the formulation is administered by oral route. However, infants, children, the elderly, or patients suffering from swallowing difficulty can not use easily the solid oral dosage forms. Therefore, the formulation according to the present invention is preferably in liquid oral dosage form, more preferably in syrup form in order to ensure a high level of patient compliance and a successful progression of the treatment.

In another aspect of the present invention, said formulation, in addition to *Hedera helix* extract, *Pelargonium sidoides* extract, and *Zingiber officinale* extract, comprises at least one of the *Propolis, Glycyrrhiza glabra*, and *Echinacea purpurea* extracts as active agents known to be useful in the treatment, prevention of various respiratory diseases or alleviation and/or elimination of symptoms thereof and also in boosting the immune system.

The formulation according to the present invention, in addition to *Hedera helix, Pelargonium sidoides*, and *Zingiber officinale* extracts, comprises at least one of the *Propolis, Glycyrrhiza glabra*, and *Echinacea purpurea* extracts preferably in the following ratios:

The weight ratio of the *Hedera helix* extract, *Pelargonium sidoides* extract, *Zingiber officinale* extract, and *Propolis* extract is 6:10:4:1, respectively;

The weight ratio of the *Hedera helix* extract, *Pelargonium sidoides* extract, *Zingiber officinale* extract, and *Glycyrrhiza glabra* extract is 7:12:5:5, respectively;

The weight ratio of the *Hedera helix* extract, *Pelargonium sidoides* extract, *Zingiber officinale* extract, and *Echinacea purpurea* extract is 7:12:5:8, respectively;

The weight ratio of the *Hedera helix* extract, *Pelargonium sidoides* extract, *Zingiber officinale* extract, *Propolis*, and *Glycyrrhiza glabra* extract is 6:10:4:1:4, respectively;

The weight ratio of the *Hedera helix* extract, *Pelargonium sidoides* extract, *Zingiber officinale* extract, *Propolis* extract, and *Echinacea purpurea* extract is 6:10:4:1:7, respectively; and The weight ratio of the *Hedera helix* extract, *Pelargonium sidoides* extract, *Zingiber officinale* extract, *Glycyrrhiza glabra* extract, and *Echinacea purpurea* extract is 7:12:5:5:8, respectively.

When the present invention comprises said plant extracts with the ratios mentioned above, as compared to the other ratios, the physical properties reaches the optimal level in terms of patient compliance and the longest duration physical stability is provided.

In another aspect of the present invention, said formulation, in addition to the herbal extracts mentioned above, comprises at least one excipient. Accordingly, the formulation according to the present invention comprises at least one pharmaceutically acceptable excipient selected from the group comprising fillers, solvents, pH adjusting agents, sweeteners, aromatic agents and preservatives.

It is likely that the excipient or excipients contained in the formulation may positively or adversely affect the characteristics, effectiveness and/or stability of the formulation by interacting with the plant extracts and/or with each other. Therefore, when excipient selection is carried out for the formulation according to the present invention, care should be taken and object of the present invention should be considered.

Suitable fillers contained in the formulation according to the present invention are selected from, the group comprising, but not limited to, sucrose, sorbitol, xylitol, dextrose, fructose, maltitol, sugar, potassium, aspartame, saccharin, saccharin sodium, spray dried or anhydrous lactose, mannitol, starch, cellulose (preferably, microcrystalline cellulose) and mixtures thereof; wherein the preferred filler is sorbitol.

Fillers are used as dispersion medium in the oral liquid formulations. In addition, they can be used to adjust the concentration of the formulation and to improve manufacturability. These excipients are preferably in solution form in the oral liquid formulations.

Sorbitol has some physical and chemical properties which make it ideal for being used as a suitable filler for the present invention. It is chemically inactive and compatible with a number of other excipients. In addition, it is dissolved easily in water, contributes to maintaining the stability of the formulation by increasing its viscosity. Besides all of the said features, sorbitol is also used as a sweetener in the pharmaceutical formulations.

In a formulation according to the present invention, it was found that when sorbitol was contained in an amount between 1% and 60% (w/v) based on the total volume of the formulation, it contributed both to improving the taste of the formulation, and to the prevention of crystallization thereof so that the homogeneity and the clarity of the formulation was maintained. The percentage amount of the sorbitol contained in the formulation according to the present invention based on the total volume of the formulation is preferably between 5% and 30% (w/v), and more preferably between 10% and 25% (w/v).

Suitable pH adjusting agents contained in the formulation according to the present invention are selected from the group comprising, but not limited to, ascorbic acid, acetic acid, tartaric acid, citric acid, sodium citrate, potassium citrate, sodium phosphate, tricalcium phosphate, calcium carbonate, sodium bicarbonate, calcium phosphates, carbonated calcium phosphates, magnesium hydroxide and hydrates thereof and mixtures thereof; wherein the preferred pH adjusting agents are citric acid monohydrate and sodium citrate dihydrate.

Within the scope of the present invention, in the event that the weight ratio of the sodium citrate dihydrate to the citric acid monohydrate is 1:2, and thus the pH level is maintained at acidic levels, it is observed that it contributes to the improvement in the taste of the formulation and also the maintenance of the physical stability thereof due to the pH value remaining constant. The percentage amount of the citric acid monohydrate provided in said formulation based on the total volume of the formulation is between 0.01% and 1% (w/v), preferably between 0.02% and 0.5% (w/v), and more preferably between 0.03% and 0.2%; the percentage amount of the sodium citrate dihydrate is between 0.005% and 0.5% (w/v), preferably between 0.01% and 0.25%, and more preferably between 0.015% and 0.1%. pH value of the formulation according to the present invention is between 2 and 6.5, preferably between 3 and 6, and more preferably between 3.5 and 5.5.

Suitable preservatives contained in the formulation according to the present invention are selected the group comprising, but not limited to, methyl paraben and propyl paraben and salts thereof (e.g. sodium, potassium), sodium benzoate, citric acid, benzoic acid, butylated hydroxytoluene and butylated hydroxyanisole, and mixtures thereof.

Here, it was surprisingly found that when the above indicated amounts of herbal extracts were added to a formulation according to the present invention, the need to include a preservative in said formulation was avoided due to the characteristic features of these extracts, particularly the antibacterial, antiviral, and/or antioxidative features of the same. Thus, when a formulation according to the present invention contains the above indicated amounts of herbal extracts, the physical stability thereof can be maintained for a longer time without containing a preservative and a more natural formulation can be obtained as compared to the formulation comprising a preservative.

Suitable aromatic agents contained in the formulation according to the present invention are selected from the group comprising, but not limited to, fruit aromas such as of orange, cherry, strawberry, banana, cherry, lemon; aromas of cardamom, anise, mint, menthol, *eucalyptus*, vanillin and ethyl vanillin, and mixtures thereof; wherein the preferred aromatic agent is *eucalyptus*.

As mentioned above, when *eucalyptus* is used as the aromatic agent, it is observed that it shows a supporting effect for said formulation due to the refreshing and smoothening effect of scent and the patients administered with said formulation feels instant relief and alleviation of symptoms, thus, it helped them feel better within a shorter period of time. It is also observed that the patient compliance is improved as well as adherence of the patients to the treatment is also accelerated due to the effect of the formulation according to the present invention comprising *eucalyptus* as the aromatic agent. In the present invention, effective results are obtained when the percentage amount of the *eucalyptus* used as the aromatic agent based on the total volume of the formulation is between 0.01% and 5% (w/v), preferably between 0.03% and 3% (w/v), and more preferably between 0.05% and 2%.

Suitable sweeteners contained in the formulation according to the present invention are selected from the group comprising, but not limited to, sucralose, ammonium glycerizinate, acesulfame-K, aspartame, saccharin or sodium and calcium salts of saccharin, sodium cyclamate, sucrose, fructose, glucose, sorbitol, and mixtures thereof. The percentage amount of the sweetener contained in the formulation according to the present invention based on the total volume of the formulation is between 0.005% and 20% (w/v), preferably between 0.005% and 15% (w/v), and more preferably between 0.005% and 10% (w/v).

Suitable solvents contained in the formulation according to the present invention are selected from the group comprising, but not limited to, water soluble polar solvents such as propylene glycol, glycerin, water, ethanol, isopropyl alcohol, and water insoluble non-polar solvents or a mixture thereof. For the ideal preparation of the formulation according to the present invention, it comprises at least 5%, preferably, at least 15% of solvent.

The formulation according to the present invention comprises preferably propylene glycol, glycerin, water or ethanol, or a mixture thereof as a solvent. When the percentage amount of ethanol contained in the formulation according to the present invention as solvent based on the total volume of the formulation is between 0.5% and 30%, preferably between 0.5% and 15%, and more preferably between 1% and 10%, it is found that it plays a role in increasing the solubility of the *Zingiber officinale* extract and thus, preventing the precipitation. Thus, in particular, by visually improving the physical properties of the formulation, a clearer and a more homogeneous formulation can be obtained and patient compliance can be increased. Said formulation, in addition to the ethanol, also comprises water, propylene glycol and glycerin as solvent. The weight ratio of propylene glycol to glycerin contained in the formulation is between 100:1 and 1:90, preferably between 10:1 and 1:20, and more preferably between 2:1 and 1:5.

The formulation according to the present invention can be used as a pharmaceutical and/or phytotherapeutic formulation and also as a food supplement.

All plant extracts comprised in the content of the formulation within the scope of the present invention can be obtained from the shell, leaf, flower, root or seed of respective plants.

Prior art methods are used for obtaining all the extracts according to the present invention.

In another aspect, the present invention provides a formulation used for the treatment, prevention of, and/or for the alleviation of the effects of parasitic diseases, skin diseases, acute and chronic respiratory tract infections, cold, pharyngitis, angina, sinusitis, acute bronchitis, tonsillitis, bronchial asthma, chronic obstructive pulmonary disease, acute and chronic airway inflammation, lower and upper respiratory tract infections, acute and chronic inflammatory bronchial diseases, infections of the ear, nose, and throat, other bacterial and viral respiratory tract diseases. Additionally, the formulation according to the present invention can be used in the alleviation and/or elimination of the symptoms resulting from said diseases, in boosting the immune system, as well as be used as an expectorant, an anti-inflammatory agent, antibacterial agent and antiviral agent, and in alleviating the symptoms like cough and the sore throat.

The formulation according to the present invention comprising herbal extracts, having improved physical stability, being preferably in the liquid oral dosage form comprises:
    a. 0.05% to 20% by weight of *Hedera helix* extract,
    b. 0.05% to 30% by weight of *Pelargonium sidoides* extract,
    c. 0.05% to 30% by weight of *Zingiber officinale* extract,
    d. 1% to 60% by weight of propylene glycol,
    e. 2% to 90% by weight of glycerin,
    f. 0.01% to 1% by weight of citric acid monohydrate,
    g. 0.005% to 0.5% by weight sodium citrate dihydrate,
    h. 1% to 60% by weight of sorbitol,
    i. 0.01% to 2% by weight of sucralose,
    j. 0.01% to 10% by weight of ammonium glycerizinate,
    k. 0.5% to 30% by weight of ethanol,
    l. 0.01% to 5% by weight of *eucalyptus*,
    m. sufficient amount of water until the total volume is 100 ml.

In another preferred embodiment of the present invention, said above mentioned formulation according to the present invention comprises:
    a. 0.1% to 15% by weight of *Hedera helix* extract,
    b. 0.1% to 20% by weight of *Pelargonium sidoides* extract,
    c. 0.1% to 20% by weight of *Zingiber officinale* extract,
    d. 5% to 30% by weight of propylene glycol,
    e. 4% to 60% by weight of glycerin,
    f. 0.02% to 0.5% by weight of citric acid monohydrate,
    g. 0.01% to 0.25% by weight sodium citrate dihydrate,
    h. 5% to 30% by weight of sorbitol,
    i. 0.01% to 2% by weight of sucralose,
    j. 0.01% to 10% by weight of ammonium glycerizinate,
    k. 0.5% to 15% by weight of ethanol,
    l. 0.03% to 3% by weight of *eucalyptus*,
    m. sufficient amount of water until the total volume is 100 ml.

In another preferred embodiment of the present invention, said above mentioned formulation according to the present invention comprises:

a. 0.25% to 10% by weight of *Hedera helix* extract,
b. 0.2% to 15% by weight of *Pelargonium sidoides* extract,
c. 0.1% to 4% by weight of *Zingiber officinale* extract,
d. 10% to 30% by weight of propylene glycol,
e. 10% to 45% by weight of glycerin,
f. 0.03% to 0.2% by weight of citric acid monohydrate,
g. 0.015% to 0.1% by weight sodium citrate dihydrate,
h. 10% to 25% by weight of sorbitol,
i. 0.01% to 2% by weight of sucralose,
j. 0.01% to 10% by weight of ammonium glycerizinate,
k. 1% to 10% by weight of ethanol,
l. 0.05% to 2% by weight of *eucalyptus*,
m. sufficient amount of water until the total volume is 100 ml.

Within the scope of the present invention, the percentage amounts of substances by weight contained in the formulation represent the gram amounts provided in the 100 ml formulation.

According to another object of the present invention, the preferred process according to the present invention for preparing the formulation comprises the following steps:
a. all solvents are added to the manufacturing vessel and mixed until a homogeneous mixture is obtained (mixture A),
b. inactive ingredients are added to the vessel containing mixture A and mixed until a homogeneous mixture is obtained (mixture B),
c. herbal substance extracts are added onto the mixture B obtained in the previous step successively and mixed until a homogeneous mixture is obtained (mixture C),
d. obtained mixture C is converted into suitable dosage forms and filled into the packages.

Another preferred process according to the present invention for preparing the formulation being preferably in liquid oral dosage form according to the present invention comprises the following steps:
a. all solvents are added to the manufacturing vessel and mixed until a homogeneous mixture is obtained (mixture A),
b. inactive ingredients are added to the vessel comprising mixture A and mixed until a homogeneous mixture is obtained (mixture B),
c. herbal substance extracts are added onto the mixture B obtained in the previous step successively and mixed until a homogeneous mixture is obtained (mixture C),
d. obtained mixture C is subjected to the filtering process and let to settle,
e. at the end of the settling period the obtained final product is filled into suitable bottles.

During the manufacturing processes described above, homogenizer and mixer are run at high speeds and mixing process is continued until a homogeneous mixture which is free of solid masses is obtained.

Experimental Studies for Evaluation of the Physical Stability

On the purpose of demonstrating stability of the formulation to be improved when it contains the combination of *Hedera helix* extract, *Pelargonium sidoides* extract and *Zingiber officinale* extract, firstly, three formulations are prepared according to the present invention. These formulations comprise:

Formulation 1: *Hedera helix* extract+excipients
Formulation 2: *Hedera helix* extract & *Pelargonium sidoides* extract+excipients
Formulation 3: *Hedera helix* extract & *Pelargonium sidoides* extract & *Zingiber officinale* extract+excipients Each of the above formulations prepared for the comparative experimental analysis comprises same excipients in the same amounts.

Examining changes in physical properties such as pH, density, viscosity, color, precipitation, taste, smell, etc of the formulations under stress conditions is useful in evaluating the physical stability of the formulations. Therefore, stress testing is carried out on the above formulations in an drying-oven at the temperature of 50° C. as a thermal condition and under conditions defined in ICH *Q1B Photostability Testing of New Drug Substances and Products* to determine the physical changes of the formulations. At specific time periods, physical analyses of the formulations are performed. Suprisingly, it has found that the formulation comprising the combination of *Hedera helix* extract, *Pelargonium sidoides* extract and *Zingiber officinale* extract is the most stable formulation among the formulations that are analysed. Comparative results obtained at the end of the stress testing are given below:

Thermal Stress Testing

Thermal stress testing is carried out on the above formulations that are kept in a drying-oven with the temperature of 50° C. throughout 10 days. During testing period, the changes in the physical properties of the formulations are determined, and comparative results obtained at the end of the testing period are given below.

pH

According to the comparative results of Table 1, the change in pH value of the Formulation 1 and Formulation 2 is higher than that of the Formulation 3 throughout the testing period. In fact, the pH values of the Formulation 3 remains almost the same throughout the testing period. It shows that the pH value of the formulation comprising the combination of *Hedera helix*, *Pelargonium sioides* and *Zingiber officinale* is more stable that that of the other formulations. Suprisingly, it has also found that while the pH value of the formulation approaches to 4, the taste of the formulation becomes better, thus, the Formulation 3 has the best taste among the formulations.

The increase occurred in the pH values of the Formulation 1 and the Formulation 2 also leads to the taste of the formulations to be changed throughout the testing period.

TABLE 1

| | pH values in the formulations versus time | | | | | | | | | | |
|---|---|---|---|---|---|---|---|---|---|---|---|
| | 0 h | 5 h | 21 h | 29 h | 44 h | 54 h | 5 d | 6 d | 8 d | 9 d | 10 d |
| Formulation 1 | 4.27 | 4.35 | 4.36 | 4.38 | 4.41 | 4.39 | 4.43 | 4.45 | 4.52 | 4.55 | 4.62 |
| Formulation 2 | 4.16 | 4.15 | 4.17 | 4.15 | 4.12 | 4.15 | 4.15 | 4.14 | 4.16 | 4.18 | 4.25 |
| Formulation 3 | 4.03 | 4.02 | 4.04 | 4.02 | 4.00 | 4.03 | 4.04 | 4.01 | 4.04 | 4.01 | 4.04 | h: hour;
d: day

The pH values of the formulations throughout the testing period are measured using Mettler Toledo/Seven Multi pH meter at room temperature (25° C.±2° C.)

Density

According to the comparative results of Table 2, the increase in density of the Formulation 1 and Formulation 2 is higher than that of the Formulation 3 throughout the testing period. As the same in the density of the formulations, the increase in the viscosity of the Formulation 1 and the Formulation 2 is higher than that of the Formulation 3 throughout the testing period that is shown in Table 3.

TABLE 2

Densities of the formulations versus time

|  | 0 d | 10 d |
| --- | --- | --- |
| Formulation 1 | 1.1289 g/mL | 1.1604 g/mL |
| Formulation 2 | 1.1315 g/mL | 1.1398 g/mL |
| Formulation 3 | 1.1323 g/mL | 1.1329 g/mL | d: day

TABLE 3

Viscosities of the formulations versus time

|  | 0 d | 10 d |
| --- | --- | --- |
| Formulation 1 | 19.2 mP | 22.1 mP |
| Formulation 2 | 21.1 mP | 21.5 mP |
| Formulation 3 | 21.9 mP | 22.0 mP | d: day

The densities of the formulations throughout the testing period are measured using Mettler Toledo DE40 density meter at room temperature (25° C.±2° C.) and the viscosities of the formulations throughout the testing period are measured using BROOKFIELD DV-II+Pro viscosity meter at room temperature (25° C.±2° C.).

Precipitation

As shown in Table 4, although the precipitation is observed in the formulation comprising *Hedera helix* alone (Formulation 1), the addition of *Pelargonium sidoides* and/or *Zingiber officinale* to the formulation comprising *Hedera helix* prevents the precipitation and provides the Formulation 2 and Formulation 3 to have a clear appearance and to maintain this clarity throughout the testing period.

TABLE 4

Precipitation in the formulations versus time

|  | 0 h | 5 h | 21 h | 29 h | 44 h | 54 h | 5 d | 6 d | 8 d | 9 d | 10 d |
| --- | --- | --- | --- | --- | --- | --- | --- | --- | --- | --- | --- |
| Formulation 1 | + | + | + | + | + | + | + | + | + | + | + |
| Formulation 2 | − | − | − | − | − | − | − | − | − | − | − |
| Formulation 3 | − | − | − | − | − | − | − | − | − | − | − | h: hour;
d: day

This physical analysis to determine whether the precipitation is occurred or not in the formulations throughout the testing period, is performed by same analyst. Additionally, the analysis of each formulation is performed on the same ground which is a white flat ground lightened with a flash light parallel to the ground.

Color

As shown in Table 5, although the color change is observed in the formulation comprising *Hedera helix* alone (Formulation 1), any color change is not observed in the formulation comprising the combination of *Pelargonium sidoides* and *Hedera helix* (Formulation 2) and in the formulation comprising the combination of *Pelargonium sidoides*, *Hedera helix* and *Zingiber officinale* (Formulation 3) throughout the testing period.

TABLE 5

Color change in the formulations versus time

|  | 0 h | 5 h | 21 h | 29 h | 44 h | 54 h | 5 d | 6 d | 8 d | 9 d | 10 d |
| --- | --- | --- | --- | --- | --- | --- | --- | --- | --- | --- | --- |
| Formulation 1 | light brown | light brown | light brown | light brown | light brown | yellow | yellow | yellow | yellow | yellow | yellow |
| Formulation 2 | brown | brown | brown | brown | brown | brown | brown | brown | brown | brown | brown |
| Formulation 3 | brown | brown | brown | brown | brown | brown | brown | brown | brown | brown | brown | h: hour; d: day

This physical analysis to determine whether the precipitation is occurred or not in the formulations throughout the testing period, is performed by same analyst. Additionally, the analysis of each formulation is performed on the same ground which is a white flat ground lightened with a flash light parallel to the ground, and the color of the formulations is decided using a color scale.

Smell

It is observed that the smell of the Formulation 3 does not change whereas the smell of the other formulations change throughout the testing period. This physical analysis is also performed by same analyst in the same odorless environment for each formulation.

According to the thermal stress testing results, although the temperature at which the physical analyses are performed is high (50° C.), the Formulation 3 is less affected from the temperature in comparison with the other formulations, and thus, the physical stability of the Formulation 3 remains stable throughout the testing period.

Photostability Stress Testing

For determining the photostability of the formulations, the photostability stress testing is carried out under conditions defined in ICH *Q1B Photostability Testing of New Drug Substances and Products*. Two different conditions defined in the guideline are used during the testing period: initially formulations are kept in a photostability cabine with 200 Wh/m² at a constant temperature (25° C.) during 4 hours (ICH parameter-1). After the physical analyses of the formulations are carried out, these formulations are kept in a photostability cabine with 1.2 million lux hours at a constant temperature (25° C.) during 10 hours (ICH parameter-1).

According to the comparative results shown in Table 6, the Formulation 3 is the most photostable formulation among the formulations. The Formulation 3 is less affected from the light stress in comparison with other formulations, and thus, the change in the physical properties of the Formulation 3 is less than that of the Formulation 1 and Formulation 2 at the end of the testing periods.

TABLE 6

Photostability of the formulations

|  | ICH parameter −1 | | | | ICH parameter −2 | | | |
| --- | --- | --- | --- | --- | --- | --- | --- | --- |
|  | pH | Density (g/mL) | Precipitation | Color | pH | Density (g/mL) | Precipitation | Color |
| Formulation 1 | 4.39 | 1.1292 | + | light brown | 4.51 | 1.1396 | + | light yellow |
| Formulation 2 | 4.19 | 1.1316 | − | brown | 4.25 | 1.1312 | − | brown |
| Formulation 3 | 4.06 | 1.1332 | − | brown | 4.07 | 1.1330 | − | brown |

Consequently, these comparative results given from Table 1 to Table 6 demonstrate that the physical stability of the formulation comprising the combination of *Hedera helix*, *Pelargonium sidoides* and *Zingiber officinale* (Formulation 3) is higher than that of the formulations comprising *Hedera helix* (Formulation 1) alone or the combination of *Hedera helix* and *Pelargonium sidoides* (Formulation 2). In other words, the addition of *Zingiber officinale* to the formulation comprising the combination of *Hedera helix* and *Pelargonium sidoides* increases substantially the physical stability of the formulation. Additionally, the fact that the Formulation 3 has an improved physical stability is also an indication of having an improved chemical stability.

The present invention is further described by the following examples. The purpose of these examples is not to limit the scope of the present invention and the details thereof should be evaluated in light of the description given above.

Example 1

Solvents are mixed in the mixer until a homogeneous mixture is obtained. Then, the inactive ingredients are added thereto and mixed until a homogeneous mixture is obtained. Finally, *Hedera helix* extract, *Pelargonium sidoides* extract, and *Zingiber officinale* extract are added, respectively and mixed at high speed until a homogeneous mixture is obtained. The obtained mixture is subjected to the filtering process and let to settling. At the end of the settling period the obtained final product is filled into suitable bottles.

| Ingredients | Amount % |
| --- | --- |
| *Pelargonium sidoides* extract | 0.05%-30% |
| *Zingiber officinale* extract | 0.05%-30% |
| *Hedera helix* extract | 0.05%-20% |
| Propylene glycol | 10%-30% |
| Glycerin | 10%-45% |
| Citric acid monohydrate | 0.03%-0.2% |
| Sodium citrate dihydrate | 0.015%-0.1% |
| Sorbitol | 10%-25% |
| Sucralose | 0.01%-2% |
| Ammonium glycerizinate | 0.01%-10% |
| Ethanol | 1%-10% |
| *Eucalyptus* | 0.03%-3% |
| Water | q.s. | q.s.: Quantity sufficient (enough to complete the total volume of the formulation to 100 ml)

Example 2

Solvents are mixed in the mixer until a homogeneous mixture is obtained. Then, the inactive ingredients are added thereto and mixed until a homogeneous mixture is obtained. Finally, *Hedera helix* extract, *Pelargonium sidoides* extract, and *Zingiber officinale* extract are added, respectively and mixed at high speed until a homogeneous mixture is obtained. The obtained mixture is subjected to the filtering process and let to settling. At the end of the settling period the obtained final product is filled into suitable bottles.

| Ingredients | Amount % |
| --- | --- |
| *Pelargonium sidoides* extract | 0.2%-15% |
| *Zingiber officinale* extract | 0.2%-10% |
| *Hedera helix* extract | 0.25%-10% |
| Propylene glycol | 1%-60% |
| Glycerin | 2%-90% |
| Citric acid monohydrate | 0.01%-1% |
| Sodium citrate dihydrate | 0.005%-0.5% |
| Sorbitol | 1%-60% |
| Sucralose | 0.01%-2% |
| Ammonium glycerizinate | 0.01%-10% |
| Ethanol | 0.5%-30% |
| *Eucalyptus* | 0.01%-5% |
| Water | q.s. | q.s.: Quantity sufficient (enough to complete the total volume of the formulation to 100 ml)

Example 3

Solvents are mixed in the mixer until a homogeneous mixture is obtained. Then, the inactive ingredients are added thereto and mixed until a homogeneous mixture is obtained. Finally, *Hedera helix* extract, *Pelargonium sidoides* extract, *Zingiber officinale* extract, and *Propolis* extract are added, respectively and mixed at high speed until a homogeneous mixture is obtained. The obtained mixture is subjected to the

| Ingredients | Amount % |
|---|---|
| *Pelargonium sidoides* extract | 0.05%-30% |
| Propolis extract | 0.02%-30% |
| *Zingiber officinale* extract | 0.05%-30% |
| *Hedera helix* extract | 0.05%-20% |
| Propylene glycol | 1%-60% |
| Glycerin | 2%-90% |
| Citric acid monohydrate | 0.01%-1% |
| Sodium citrate dihydrate | 0.005%-0.5% |
| Sorbitol | 1%-60% |
| Sucralose | 0.01%-2% |
| Ammonium glycerizinate | 0.01%-10% |
| Ethanol | 0.5%-30% |
| *Eucalyptus* | 0.01%-5% |
| Water | q.s. | q.s.: Quantity sufficient (enough to complete the total volume of the formulation to 100 ml)

filtering process and let to settling. At the end of the settling period the obtained final product is filled into suitable bottles.

Example 4

Solvents are mixed in the mixer until a homogeneous mixture is obtained. Then, the inactive ingredients are added thereto and mixed until a homogeneous mixture is obtained. Finally, *Hedera helix* extract, *Pelargonium sidoides* extract, *Zingiber officinale* extract, and Propolis extract are added, respectively and mixed at high speed until a homogeneous mixture is obtained. The obtained mixture is subjected to the filtering process and let to settling. At the end of the settling period the obtained final product is filled into suitable bottles.

| Ingredients | Amount % |
|---|---|
| *Pelargonium sidoides* extract | 0.2%-15% |
| Propolis extract | 0.05%-10% |
| *Zingiber officinale* extract | 0.1%-4% |
| *Hedera helix* extract | 0.25%-10% |
| Propylene glycol | 10%-30% |
| Glycerin | 10%-45% |
| Citric acid monohydrate | 0.03%-0.2% |
| Sodium citrate dihydrate | 0.015%-0.1% |
| Sorbitol | 10%-25% |
| Sucralose | 0.01%-2% |
| Ammonium glycerizinate | 0.01%-10% |
| Ethanol | 1%-10% |
| *Eucalyptus* | 0.05%-2% |
| Water | q.s. | q.s.: Quantity sufficient (enough to complete the total volume of the formulation to 100 ml)

Example 5

Solvents are mixed in the mixer until a homogeneous mixture is obtained. Then, the inactive ingredients are added thereto and mixed until a homogeneous mixture is obtained. Finally, *Hedera helix* extract, *Pelargonium sidoides* extract, *Zingiber officinale* extract, and *Glycyrrhiza glabra* extract are added, respectively and mixed at high speed until a homogeneous mixture is obtained. The obtained mixture is subjected to the filtering process and let to settling. At the end of the settling period the obtained final product is filled into suitable bottles.

| Ingredients | Amount % |
|---|---|
| *Pelargonium sidoides* extract | 0.05%-30% |
| *Glycyrrhiza glabra* extract | 0.01%-20% |
| *Zingiber officinale* extract | 0.05%-30% |
| *Hedera helix* extract | 0.05%-20% |
| Propylene glycol | 1%-60% |
| Glycerin | 2%-90% |
| Citric acid monohydrate | 0.01%-1% |
| Sodium citrate dihydrate | 0.005%-0.5% |
| Sorbitol | 1%-60% |
| Sucralose | 0.01%-2% |
| Ammonium glycerizinate | 0.01%-10% |
| Ethanol | 0.5%-30% |
| *Eucalyptus* | 0.01%-5% |
| Water | q.s. | q.s.: Quantity sufficient (enough to complete the total volume of the formulation to 100 ml)

Example 6

Solvents are mixed in the mixer until a homogeneous mixture is obtained. Then, the inactive ingredients are added thereto and mixed until a homogeneous mixture is obtained. Finally, *Hedera helix* extract, *Pelargonium sidoides* extract, *Zingiber officinale* extract, and *Glycyrrhiza glabra* extract are added, respectively and mixed at high speed until a homogeneous mixture is obtained. The obtained mixture is subjected to the filtering process and let to settling. At the end of the settling period the obtained final product is filled into suitable bottles.

| Ingredients | Amount % |
|---|---|
| *Pelargonium sidoides* extract | 0.2%-15% |
| *Glycyrrhiza glabra* extract | 0.10%-10% |
| *Zingiber officinale* extract | 0.1%-4% |
| *Hedera helix* extract | 0.25%-10% |
| Propylene glycol | 10%-30% |
| Glycerin | 10%-45% |
| Citric acid monohydrate | 0.03%-0.2% |
| Sodium citrate dihydrate | 0.015%-0.1% |
| Sorbitol | 10%-25% |
| Sucralose | 0.01%-2% |
| Ammonium glycerizinate | 0.01%-10% |
| Ethanol | 1%-10% |
| *Eucalyptus* | 0.05%-2% |
| Water | q.s. | q.s.: Quantity sufficient (enough to complete the total volume of the formulation to 100 ml)

Example 7

Solvents are mixed in the mixer until a homogeneous mixture is obtained. Then, the inactive ingredients are added thereto and mixed until a homogeneous mixture is obtained. Finally, *Hedera helix* extract, *Pelargonium sidoides* extract, *Zingiber officinale* extract, and *Echinacea purpurea* extract are added, respectively and mixed at high speed until a homogeneous mixture is obtained. The obtained mixture is subjected to the filtering process and let to settling. At the end of the settling period the obtained final product is filled into suitable bottles.

| Ingredients | Amount % |
|---|---|
| *Pelargonium sidoides* extract | 0.05%-30% |
| *Echinacea purpurea* extract | 0.1%-80% |
| *Zingiber officinale* extract | 0.05%-30% |

| Ingredients | Amount % |
| --- | --- |
| *Hedera helix* extract | 0.05%-20% |
| Propylene glycol | 1%-60% |
| Glycerin | 2%-90% |
| Citric acid monohydrate | 0.01%-1% |
| Sodium citrate dihydrate | 0.005%-0.5% |
| Sorbitol | 1%-60% |
| Sucralose | 0.01%-2% |
| Ammonium glycerizinate | 0.01%-10% |
| Ethanol | 0.5%-30% |
| *Eucalyptus* | 0.01%-5% |
| Water | q.s. | q.s.: Quantity sufficient (enough to complete the total volume of the formulation to 100 ml)

Example 8

Solvents are mixed in the mixer until a homogeneous mixture is obtained. Then, the inactive ingredients are added thereto and mixed until a homogeneous mixture is obtained. Finally, *Hedera helix* extract, *Pelargonium sidoides* extract, *Zingiber officinale* extract, and *Echinacea purpurea* extract are added, respectively and mixed at high speed until a homogeneous mixture is obtained. The obtained mixture is subjected to the filtering process and let to settling. At the end of the settling period the obtained final product is filled into suitable bottles.

| Ingredients | Amount % |
| --- | --- |
| *Pelargonium sidoides* extract | 0.2%-15% |
| *Echinacea purpurea* extract | 0.5%-40% |
| *Zingiber officinale* extract | 0.1%-4% |
| *Hedera helix* extract | 0.25%-10% |
| Propylene glycol | 10%-30% |
| Glycerin | 10%-45% |
| Citric acid monohydrate | 0.03%-0.2% |
| Sodium citrate dihydrate | 0.015%-0.1% |
| Sorbitol | 10%-25% |
| Sucralose | 0.01%-2% |
| Ammonium glycerizinate | 0.01%-10% |
| Ethanol | 1%-10% |
| *Eucalyptus* | 0.05%-2% |
| Water | q.s. | q.s.: Quantity sufficient (enough to complete the total volume of the formulation to 100 ml)

Example 9

Solvents are mixed in the mixer until a homogeneous mixture is obtained. Then, the inactive ingredients are added thereto and mixed until a homogeneous mixture is obtained. Finally, *Hedera helix* extract, *Pelargonium sidoides* extract, *Zingiber officinale* extract, *Propolis* extract, and *Echinacea purpurea* extract are added, respectively and mixed at high speed until a homogeneous mixture is obtained. The obtained mixture is subjected to the filtering process and let to settling. At the end of the settling period the obtained final product is filled into suitable bottles.

| Ingredients | Amount % |
| --- | --- |
| *Pelargonium sidoides* extract | 0.05%-30% |
| *Echinacea purpurea* extract | 0.1%-80% |
| Propolis extract | 0.02%-30% |
| *Zingiber officinale* extract | 0.05%-30% |
| *Hedera helix* extract | 0.05%-20% |

| Ingredients | Amount % |
| --- | --- |
| Propylene glycol | 1%-60% |
| Glycerin | 2%-90% |
| Citric acid monohydrate | 0.01%-1% |
| Sodium citrate dihydrate | 0.005%-0.5% |
| Sorbitol | 1%-60% |
| Sucralose | 0.01%-2% |
| Ammonium glycerizinate | 0.01%-10% |
| Ethanol | 0.5%-30% |
| *Eucalyptus* | 0.01%-5% |
| Water | q.s. | q.s.: Quantity sufficient (enough to complete the total volume of the formulation to 100 ml)

Example 10

Solvents are mixed in the mixer until a homogeneous mixture is obtained. Then, the inactive ingredients are added thereto and mixed until a homogeneous mixture is obtained. Finally, *Hedera helix* extract, *Pelargonium sidoides* extract, *Zingiber officinale* extract, *Propolis* extract, and *Echinacea purpurea* extract are added, respectively and mixed at high speed until a homogeneous mixture is obtained. The obtained mixture is subjected to the filtering process and let to settling. At the end of the settling period the obtained final product is filled into suitable bottles.

| Ingredients | Amount % |
| --- | --- |
| *Pelargonium sidoides* extract | 0.2%-15% |
| *Echinacea purpurea* extract | 0.5%-40% |
| Propolis extract | 0.05%-10% |
| *Zingiber officinale* extract | 0.1%-4% |
| *Hedera helix* extract | 0.25%-10% |
| Propylene glycol | 10%-30% |
| Glycerin | 10%-45% |
| Citric acid monohydrate | 0.03%-0.2% |
| Sodium citrate dihydrate | 0.015%-0.1% |
| Sorbitol | 10%-25% |
| Sucralose | 0.01%-2% |
| Ammonium glycerizinate | 0.01%-10% |
| Ethanol | 1%-10% |
| *Eucalyptus* | 0.05%-2% |
| Water | q.s. | q.s.: Quantity sufficient (enough to complete the total volume of the formulation to 100 ml)

Example 11

Solvents are mixed in the mixer until a homogeneous mixture is obtained. Then, the inactive ingredients are added thereto and mixed until a homogeneous mixture is obtained. Finally, *Hedera helix* extract, *Pelargonium sidoides* extract, *Zingiber officinale* extract, *Glycyrrhiza glabra* extract, and *Echinacea purpurea* extract are added, respectively and mixed at high speed until a homogeneous mixture is obtained. The obtained mixture is subjected to the filtering process and let to settling. At the end of the settling period the obtained final product is filled into suitable bottles.

| Ingredients | Amount % |
| --- | --- |
| *Pelargonium sidoides* extract | 0.05%-30% |
| *Echinacea purpurea* extract | 0.1%-80% |
| *Glycyrrhiza glabra* extract | 0.01%-20% |
| *Zingiber officinale* extract | 0.05%-30% |
| *Hedera helix* extract | 0.05%-20% |

-continued

| Ingredients | Amount % |
|---|---|
| Propylene glycol | 1%-60% |
| Glycerin | 2%-90% |
| Citric acid monohydrate | 0.01%-1% |
| Sodium citrate dihydrate | 0.005%-0.5% |
| Sorbitol | 1%-60% |
| Sucralose | 0.01%-2% |
| Ammonium glycerizinate | 0.01%-10% |
| Ethanol | 0.5%-30% |
| *Eucalyptus* | 0.01%-5% |
| Water | q.s. | q.s.: Quantity sufficient (enough to complete the total volume of the formulation to 100 ml)

Example 12

Solvents are mixed in the mixer until a homogeneous mixture is obtained. Then, the inactive ingredients are added thereto and mixed until a homogeneous mixture is obtained. Finally, *Hedera helix* extract, *Pelargonium sidoides* extract, *Zingiber officinale* extract, *Glycyrrhiza glabra* extract, and *Echinacea purpurea* extract are added, respectively and mixed at high speed until a homogeneous mixture is obtained. The obtained mixture is subjected to the filtering process and let to settling. At the end of the settling period the obtained final product is filled into suitable bottles.

| Ingredients | Amount % |
|---|---|
| *Pelargonium sidoides* extract | 0.2%-15% |
| *Echinacea purpurea* extract | 0.5%-40% |
| *Glycyrrhiza glabra* extract | 0.10%-10% |
| *Zingiber officinale* extract | 0.1%-4% |
| *Hedera helix* extract | 0.25%-10% |
| Propylene glycol | 10%-30% |
| Glycerin | 10%-45% |
| Citric acid monohydrate | 0.03%-0.2% |
| Sodium citrate dihydrate | 0.015%-0.1% |
| Sorbitol | 10%-25% |
| Sucralose | 0.01%-2% |
| Ammonium glycerizinate | 0.01%-10% |
| Ethanol | 1%-10% |
| *Eucalyptus* | 0.05%-2% |
| Water | q.s. | q.s.: Quantity sufficient (enough to complete the total volume of the formulation to 100 ml)

Example 13

Solvents are mixed in the mixer until a homogeneous mixture is obtained. Then, the inactive ingredients are added thereto and mixed until a homogeneous mixture is obtained. Finally, *Hedera helix* extract, *Pelargonium sidoides* extract, *Zingiber officinale* extract, *Glycyrrhiza glabra* extract, and *Propolis* extract are added, respectively and mixed at high speed until a homogeneous mixture is obtained. The obtained mixture is subjected to the filtering process and let to settling. At the end of the settling period the obtained final product is filled into suitable bottles.

| Ingredients | Amount % |
|---|---|
| *Pelargonium sidoides* extract | 0.05%-30% |
| Propolis extract | 0.02%-30% |
| *Glycyrrhiza glabra* extract | 0.01%-20% |
| *Zingiber officinale* extract | 0.05%-30% |
| *Hedera helix* extract | 0.05%-20% |

-continued

| Ingredients | Amount % |
|---|---|
| Propylene glycol | 1%-60% |
| Glycerin | 2%-90% |
| Citric acid monohydrate | 0.01%-1% |
| Sodium citrate dihydrate | 0.005%-0.5% |
| Sorbitol | 1%-60% |
| Sucralose | 0.01%-2% |
| Ammonium glycerizinate | 0.01%-10% |
| Ethanol | 0.5%-30% |
| *Eucalyptus* | 0.01%-5% |
| Water | q.s. | q.s.: Quantity sufficient (enough to complete the total volume of the formulation to 100 ml)

Example 14

Solvents are mixed in the mixer until a homogeneous mixture is obtained. Then, the inactive ingredients are added thereto and mixed until a homogeneous mixture is obtained. Finally, *Hedera helix* extract, *Pelargonium sidoides* extract, *Zingiber officinale* extract, *Glycyrrhiza glabra* extract, and *Propolis* extract are added, respectively and mixed at high speed until a homogeneous mixture is obtained. The obtained mixture is subjected to the filtering process and let to settling. At the end of the settling period the obtained final product is filled into suitable bottles.

| Ingredients | Amount % |
|---|---|
| *Pelargonium sidoides* extract | 0.2%-15% |
| Propolis extract | 0.05%-10% |
| *Glycyrrhiza glabra* extract | 0.10%-10% |
| *Zingiber officinale* extract | 0.1%-4% |
| *Hedera helix* extract | 0.25%-10% |
| Propylene glycol | 10%-30% |
| Glycerin | 10%-45% |
| Citric acid monohydrate | 0.03%-0.2% |
| Sodium citrate dihydrate | 0.015%-0.1% |
| Sorbitol | 10%-25% |
| Sucralose | 0.01%-2% |
| Ammonium glycerizinate | 0.01%-10% |
| Ethanol | 1%-10% |
| *Eucalyptus* | 0.05%-2% |
| Water | q.s. | q.s.: Quantity sufficient (enough to complete the total volume of the formulation to 100 ml)

The invention claimed is:

1. A formulation for treating or preventing a respiratory tract disease comprising effective amounts of a *Hedera helix* extract, a *Pelargonium sidoides* extract, and a *Zingiber officinale* extract, wherein the percentage amount of the *Hedera helix* extract based on the total volume of the formulation is between 0.05% and 20% (w/v); the percentage amount of the *Pelargonium* sidoides extract based on the total volume of the formulation is between 0.05% and 30% (w/v); and the percentage amount of the *Zingiber officinale* extract based on the total volume of the formulation is between 0.05% and 30% (w/v).

2. The formulation according to claim 1, wherein the percentage amount of the *Zingiber officinale* extract based on the total volume of the formulation is between 0.1% and 20% (w/v), and more preferably between 0.1% and 4% (w/v).

3. The formulation according to claim 1, wherein the weight ratio of the *Zingiber officinale* extract to the *Hedera helix* extract is between 1:0.1 and 1:50, preferably between 1:0.2 and 1:25, and more preferably between 1:0.6 and 1:15.

4. The formulation according to claim 1, wherein said formulation is administered by oral, parenteral, ocular, nasal, buccal, sublingual and topical route, and the route preferably is oral.

5. The formulation according to claim 4, wherein the route is oral and the formulation is preferably in a liquid oral dosage form, more preferably in the form of syrup.

6. The formulation according claim 1, further comprising at least one of *Propolis, Glycyrrhiza glabra*, and *Echinacea purpurea* extracts.

7. The formulation according to claim 6, wherein said formulation comprises *Hedera helix* extract, *Pelargonium sidoides* extract, *Zingiber officinale* extract, and *Propolis* extract.

8. The formulation according to claim 7, wherein the weight ratio of the *Hedera helix* extract, *Pelargonium sidoides* extract, *Zingiber officinale* extract, and *Propolis* extract is 6:10:4:1, respectively.

9. The formulation according to claim 6, wherein said formulation comprises *Hedera helix* extract, *Pelargonium sidoides* extract, *Zingiber officinale* extract, and *Glycyrrhiza glabra* extract.

10. The formulation according to claim 9, wherein the weight ratio of the *Hedera helix* extract, *Pelargonium sidoides* extract, *Zingiber officinale* extract, and *Glycyrrhiza glabra* extract is 7:12:5:5, respectively.

11. The formulation according to claim 6, wherein said formulation comprises *Hedera helix* extract, *Pelargonium sidoides* extract, *Zingiber officinale* extract, and *Echinacea purpurea* extract.

12. The formulation according to claim 11, wherein the weight ratio of *Hedera helix* extract, *Pelargonium sidoides* extract, *Zingiber officinale* extract, and *Echinacea purpurea* extract is 7:12:5:8, respectively.

13. The formulation according to claim 6, wherein said formulation comprises *Hedera helix* extract, *Pelargonium sidoides* extract, *Zingiber officinale* extract, *Propolis* extract, and *Glycyrrhiza glabra* extract.

14. The formulation according to claim 13, wherein the weight ratio of the *Hedera helix* extract, *Pelargonium sidoides* extract, *Zingiber officinale* extract, *Propolis* extract, and *Glycyrrhiza glabra* extract is 6:10:4:1:4, respectively.

15. The formulation according to claim 6, wherein said formulation comprises *Hedera helix* extract, *Pelargonium sidoides* extract, *Zingiber officinale* extract, *Propolis* extract, and *Echinacea purpurea* extract.

16. The formulation according to claim 15, wherein the weight ratio of *Hedera helix* extract, *Pelargonium sidoides* extract, *Zingiber officinale* extract, *Propolis* extract, and *Echinacea purpurea* extract is 6:10:4:1:7, respectively.

17. The formulation according to claim 6, wherein said formulation comprises *Hedera helix* extract, *Pelargonium sidoides* extract, *Zingiber officinale* extract, *Glycyrrhiza glabra* extract, and *Echinacea purpurea* extract.

18. The formulation according to claim 17, wherein the weight ratio of *Hedera helix* extract, *Pelargonium sidoides* extract, *Zingiber officinale* extract, *Glycyrrhiza glabra* extract, and *Echinacea purpurea* extract is 7:12:5:5:8, respectively.

19. The formulation according to claim 1, wherein said formulation comprises at least one pharmaceutically acceptable excipient selected from the group comprising fillers, solvents, pH adjusting agents, sweeteners, aromatic agents and preservatives.

20. The formulation according to claim 19, wherein:
(a) the filler is selected from the group comprising sucrose, sorbitol, xylitol, dextrose, fructose, maltitol, sugar potassium, aspartame, saccharin, saccharin sodium, spray dried or anhydrous lactose, mannitol, starch, cellulose (preferably, microcrystalline cellulose) and mixtures thereof, wherein when the filler is sorbitol, optionally the percentage amount of the sorbitol based on the total volume of the formulation is between 1% and 60% (w/v), preferably between 5% and 30% (w/v), and more preferably between 10% and 25% (w/v);
(b) the pH adjusting agent is selected from the group comprising ascorbic acid, acetic acid, tartaric acid, citric acid, sodium citrate, potassium citrate, sodium phosphate, tricalcium phosphate, calcium carbonate, sodium bicarbonate, calcium phosphates, carbonated calcium phosphates, magnesium hydroxide and hydrates thereof and mixtures thereof, wherein when the pH adjusting agent is citric acid monohydrate and sodium citrate dehydrate, optionally the weight ratio of sodium citrate dehydrate to the citric acid monohydrate is 1:2;
(c) the aromatic agent is selected from the group comprising fruit aromas such as of orange, cherry, strawberry, banana, sourcherry, lemon; aromas of cardamom, anise, mint, menthol, *eucalyptus*, vanillin and ethyl vanillin and mixtures thereof, wherein when the aromatic agent is *eucalyptus*, optionally the percentage amount of the *eucalyptus* based on the total volume of the formulation is between 0.01% and 5% (w/v), preferably between 0.03% and 3% (w/v), and more preferably between 0.05% and 2%;
(d) the sweetener is selected from the group comprising sucralose, ammonium glycerizinate, acesulfame-K, aspartame, saccharin or sodium and calcium salts of saccharin, sodium cyclamate, sucrose, fructose, glucose, sorbitol and mixtures thereof, and optionally the percentage amount of the sweetener based on the total volume of the formulation is between 0.005% and 20% (w/v), preferably between 0.005% and 15% (w/v), and more preferably between 0.005% and 10% (w/v); and/or
(e) the solvent is selected from the group comprising water soluble polar solvents such as propylene glycol, glycerin, water, ethanol, isopropyl alcohol and water insoluble non-polar solvents or a mixture thereof; or said formulation comprises propylene glycol, glycerin, water or ethanol, or a mixture thereof as the solvent, and optionally comprises ethanol as the solvent with the percentage amount, based on the total volume of the formulation, between 0.5% and 30%, preferably between 0.5% and 15%, and more preferably between 1% and 10%, or optionally comprises propylene glycol, glycerin, water and ethanol mixture as the solvent with the ethanol percentage amount, based on the total volume of the formulation, between 0.5% and 30%, preferably between 0.5% and 15%, and more preferably between 1% and 10%; and the weight ratio of propylene glycol to glycerin is between 100:1 and 1:90, preferably between 10:1 and 1:20, and more preferably between 2:1 and 1:5.

21. A method for preparing the formulation according to claim 1, comprising:
a. adding at least two solvents in a manufacturing vessel and mixing the solvents to form homogenous mixture A, wherein the at least two solvents are selected from the group consisting of propylene glycol, glycerin, water, ethanol, isopropyl alcohol, and water;

b. adding inactive ingredients to the manufacturing vessel containing mixture A and mixing the inactive ingredients with mixture A to form homogenous mixture B, wherein the inactive ingredients comprise at least one filler, at least one pH adjusting agent, at least one sweetener, and at least one aromatic agent;

c. adding the *Hedera helix* extract, the *Pelargonium sidoides* extract, and the *Zingiber officinale* extract to the manufacturing vessel containing mixture B and mixing the extracts with mixture B to form homogenous mixture C, d. converting mixture C into suitable dosage forms and filling into packages; or subjecting mixture C to a filtering process and subjecting filtered mixture C to a settling period to form a final product, wherein the final product is filled into suitable bottles.

22. A method of treating or preventing a respiratory tract disease in a subject in need thereof, or alleviating or eliminating a symptom thereof, the method comprising administering an effective amount of the formulation of claim 1 to the subject.

\* \* \* \* \*